(12) United States Patent
Gijsbers et al.

(10) Patent No.: US 10,548,496 B2
(45) Date of Patent: Feb. 4, 2020

(54) SYSTEM FOR PROVIDING AN ELECTRICAL ACTIVITY MAP

(75) Inventors: Gerardus Henricus Maria Gijsbers, Liempde (NL); Hendrikus Bernardus Van Den Brink, Eindhoven (NL); Sander Slegt, Best (NL); Niels Nijhof, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1327 days.

(21) Appl. No.: 13/984,313

(22) PCT Filed: Feb. 14, 2012

(86) PCT No.: PCT/IB2012/050650
§ 371 (c)(1),
(2), (4) Date: Mar. 11, 2014

(87) PCT Pub. No.: WO2012/110940
PCT Pub. Date: Aug. 23, 2012

(65) Prior Publication Data
US 2015/0038862 A1 Feb. 5, 2015

(30) Foreign Application Priority Data
Feb. 17, 2011 (EP) .................................... 11154871

(51) Int. Cl.
*A61B 5/0402* (2006.01)
*A61B 8/00* (2006.01)
(Continued)

(52) U.S. Cl.
CPC .......... *A61B 5/0402* (2013.01); *A61B 5/0408* (2013.01); *A61B 5/04085* (2013.01);
(Continued)

(58) Field of Classification Search
CPC . A61B 5/0402; A61B 5/0408; A61B 5/04085; A61B 5/065; A61B 5/6805;
(Continued)

(56) References Cited

U.S. PATENT DOCUMENTS 7,187,745 B2 * 3/2007 Flohr et al. ..................... 378/8
7,266,408 B2 9/2007 Bojovic
(Continued)

FOREIGN PATENT DOCUMENTS

EP 0735500 10/1996

OTHER PUBLICATIONS

L.K. Cheng et al., "Construction of Patient Specific Geometries Suitable for the Inverse Problem of Electrocardiography", proceedings of the 2005 IEEE Engineering in Medicine and Biology 27th Annual Conference, Shanghai, China, Sep. 1-4, 2005, pp. 7201-7203.
(Continued)

*Primary Examiner* — Alyssa M Alter

(57) ABSTRACT

The invention relates to a system for providing an electrical cardiac activity map by means of electrical signals acquired by a plurality of surface electrodes on an outer surface of a living being (6). A cardiac structure position determination unit (12) determines a position of a cardiac structure, in particular, of the epicardial surface, based on provided projection images, wherein an anatomical cardiac model is adapted to the projection images. The projection images may be provided by an x-ray C-arm system (2). An electrical activity map determination unit (13) determines the electrical activity map at the cardiac structure based on the electrical signals, the positions of the plurality of surface electrodes also determined from the projection images, and the determined position of the cardiac structure. This allows determining the electrical activity map at the cardiac struc-
(Continued)

ture with high accuracy, without necessarily needing, for instance, an x-ray computed tomography system that would apply a relatively high x-ray radiation dose to the living being. The electrodes may be comprised in a vest (8).

20 Claims, 3 Drawing Sheets

(51) Int. Cl.
| | |
|---|---|
| *A61B 5/0408* | (2006.01) |
| *A61B 5/06* | (2006.01) |
| *A61B 6/00* | (2006.01) |
| *A61B 6/02* | (2006.01) |
| *A61B 5/00* | (2006.01) |
| *A61B 8/08* | (2006.01) |
| *A61B 8/12* | (2006.01) |

(52) U.S. Cl.
CPC .............. *A61B 5/065* (2013.01); *A61B 5/684* (2013.01); *A61B 5/6805* (2013.01); *A61B 6/00* (2013.01); *A61B 6/02* (2013.01); *A61B 6/4441* (2013.01); *A61B 6/503* (2013.01); *A61B 8/0883* (2013.01); *A61B 8/12* (2013.01); *A61B 8/4254* (2013.01); *A61B 2576/023* (2013.01)

(58) Field of Classification Search
CPC ......... A61B 6/00; A61B 5/684; A61B 6/4441; A61B 6/503; A61B 2576/23; A61B 8/0883; A61B 8/12; A61B 8/4254; A61B 6/02
USPC ......................................................... 600/509
See application file for complete search history.

(56) References Cited

U.S. PATENT DOCUMENTS

| | | |
|---|---|---|
| 7,471,973 B2 | 12/2008 | Rudy et al. |
| 7,988,639 B2 | 8/2011 | Starks |
| 2003/0018277 A1 | 1/2003 | He |
| 2003/0120163 A1 | 6/2003 | Rudy |
| 2010/0191131 A1 | 7/2010 | Revishvili et al. |
| 2010/0217116 A1 | 8/2010 | Eck |

OTHER PUBLICATIONS

R.N. Ghanem et al., "Heart-Surface Reconstruction and ECG Electrodes Localization Using Fluoroscopy, Epipolar Geometry and Stereovision: Application to Noninvasive Imaging of Cardiac Electrical Activity", IEEE Transactions on Medical Imaging, vol. 22, No. 10, Oct. 2003, pp. 1307-1318.

B.M. Horacek et al., "Heart-Surface Potentials Estimated from 12-Lead Electrocardiograms", Computing in Cardiology, vol. 37, Sep. 26, 2010, pp. 37-40.

S.M. Szilagyi et al., "3D Heart Simulation and Recognition of Various Events", Proceedings of the 2005 IEEE Engineering in Medicine and Biology 27th Annual International Conference, Shanghai China, Sep. 1, 2005, pp. 4028-4041.

Cuculich et al: "Noninvasive Characterization of Epicardial Activation in Humans With Diverse Atrial Fibrillation Patterns"; Circulation, Oct. 2010, pp. 1364-1372.

Jia et al: "Electrocardiographic Imaging of Cardiac Resynchronization Therapy in Heart Failure: Observation of Variable Electrophysiologic Responses"; Heart Rhythm 2006, vol. 3, pp. 296-310.

Ramanathan et al: "Noninvasive Electrocardiographic Imaging for Cardiac Electrophysio9logyt and Arrhythmia"; Nature Medicine, vol. 10, No. 4, Apr. 2004, pp. 422-428.

Wang et al: "Electrocardiographic Imaging of Ventricular Bigeminy in a Human Subject"; Circulation Arrhythmia and Electrophysiology, 2008, 3 Page Document.

\* cited by examiner

SYSTEM FOR PROVIDING AN ELECTRICAL ACTIVITY MAP

CROSS-REFERENCE TO PRIOR APPLICATIONS

This application is the U.S. National Phase application under 35 U.S.C. § 371 of International Application Serial No. PCT/IB2012/050650, filed on Feb. 14, 2012, which claims the benefit of European Application Serial No. 11154871.5, filed on Feb. 17, 2011. These applications are hereby incorporated by reference herein.

FIELD OF THE INVENTION

The invention relates to a system, a method and a computer program for providing an electrical activity map of the heart of a living being by means of electrical signals from the heart acquired by a plurality of surface electrodes on an outer surface of the living being.

BACKGROUND OF THE INVENTION

U.S. Pat. No. 7,471,973 B2 discloses a system comprising an electrode vest with surface electrodes for measuring electrical potentials on an outer surface of a person. The system further comprises a reconstruction unit for reconstructing epicardial electrical potentials based on i) the geometry between a heart surface and the outer surface of the person and ii) the measured electrical potentials. In order to determine the geometry between the heart surface and the outer surface of the person a first projection matrix is determined based on a first imaging device and a second projection matrix is determined based on a second imaging device. At least one first two-dimensional image of the heart is obtained by using the first imaging device, at least one second two-dimensional image of the heart is obtained by using the second imaging device, and a contour of the heart in the first two-dimensional image and a contour of the heart in the second two-dimensional image are determined. Three-dimensional data associated with the heart surface are reconstructed based on the two contours, the first projection matrix and the second projection matrix, and the heart surface is registered with the outer surface of the person. The geometry between the heart surface and the outer surface of the person is finally determined by employing a boundary element method.

This system has the drawback that the quality of the determined geometry between the heart surface and the outer surface of the person may be reduced, which may lead to a reduced accuracy of the epicardial electrical potentials that are determined based on this geometry.

SUMMARY OF THE INVENTION

It is an object of the present invention to provide a system, a method and a computer program for providing an electrical activity map of the heart of a living being by means of electrical signals from the heart acquired by a plurality of surface electrodes on an outer surface of the living being, wherein the provided electrical activity map has an improved quality.

In a first aspect of the present invention a system for providing an electrical activity map of the heart of a living being by means of electrical signals from the heart acquired by a plurality of surface electrodes on an outer surface of the living being is presented, the system comprising:

a projection images providing unit for providing projection images of the heart and of the plurality of surface electrodes in different directions, a surface electrodes positions determination unit for determining positions of the plurality of surface electrodes based on the provided projection images, a cardiac structure position determination unit for determining a position of a cardiac structure of the living being based on the provided projection images, wherein the cardiac structure position determination unit is adapted to adapt an anatomical cardiac model including the cardiac structure to the provided projection images of the heart, in order to determine the position of the cardiac structure, an electrical activity map determination unit for determining the electrical activity map at the cardiac structure based on the electrical signals measured on the outer surface of the living being, the determined positions of the plurality of surface electrodes and the determined position of the cardiac structure.

Since the position of the cardiac structure of the living being is determined by adapting an anatomical cardiac model including the cardiac structure to the provided projection images of the heart, the position of the cardiac structure can be determined with a relatively high accuracy by just using a few projection images. Moreover, since the position of the cardiac structure can be determined with this high accuracy, also the electrical activity map at the cardiac structure, which is determined based on a) the electrical signals measured on the outer surface of the living being, b) the determined positions of the plurality of electrodes and c) the determined position of the cardiac structure, can be determined with increased accuracy, thereby increasing the quality of the determined electrical activity map.

The cardiac structure is preferentially the epicardial surface of the heart. The electrical activity map determination unit is therefore preferentially adapted to determine the electrical activity map on the epicardial surface of the heart based on the electrical signals measured on the outer surface of the living being, the determined positions of the plurality of electrodes and the determined position of the epicardial surface of the heart.

If the cardiac structure is three-dimensional, in particular, if the cardiac structure is the three-dimensional epicardial surface, the position of the cardiac structure preferentially defines the position of each point of the cardiac structure at which the electrical activity map should be determined. Thus, for instance, if the cardiac structure position determination unit determines the position of the epicardial surface, it determines at least the positions of the points on the epicardial surface for which an electrical potential should be determined for generating the electrical activity map.

The plurality of surface electrodes can be regarded as being an element of the system or it can be regarded as being a separate element, wherein the system is adapted to use the electrical signals of the surface electrodes for providing the electrical activity map.

The plurality of surface electrodes can be incorporated in a vest that can be worn by the living being. The living being is preferentially a person, but the living being can also be an animal.

The surface electrodes positions determination unit is preferentially adapted to determine the three-dimensional positions of the surface electrodes from two or more provided two-dimensional projection images being preferentially two-dimensional x-ray projection images. It can be adapted to provide a model distribution of the surface electrodes, to adapt the model distribution to the provided projection images and to determine the positions of the plurality of surface electrodes from the adapted model distribution. This allows determining the positions of the surface electrodes with high accuracy only based on the already provided projection images.

The cardiac model is preferentially a non-specific cardiac model. The non-specific cardiac model is an anatomical cardiac model, which is not specific to the respective living being, in particular, which is not specific to the respective person.

The cardiac structure position determination unit is preferentially adapted to adapt the anatomical cardiac model including the cardiac structure to the provided projection images of the heart by performing at least one of a translation procedure, a rotation procedure and a scaling procedure. Thus, in an embodiment the cardiac structure position determination unit can be adapted to just position and optionally scale a non-specific cardiac model such that it corresponds to the provided projection images, without modifying the shape of the cardiac model. This allows adapting the anatomical cardiac model to the provided projection images very fast. In another embodiment, also the shape of the anatomical cardiac model can be modified, in order to adapt the anatomical cardiac model to the provided projection images. For instance, the anatomical cardiac model can be stretched or compressed in certain directions for adapting the anatomical cardiac model to the provided projection images.

It is further preferred that the projection image providing unit is an x-ray C-arm system. The x-ray C-arm system allows acquiring projection images in different directions in a relatively simple way. The x-ray C-arm system can be adapted to perform a single axis C-arm movement or a dual axes C-arm movement. Moreover, the x-ray C-arm system can be a monoplane projection system or a biplane projection system. A biplane projection system can simultaneously acquire projection images in different directions. A monoplane projection system can be rotated with respect to the living being, in order to acquire the projection images in different directions.

In an embodiment, the projection images providing unit is a C-arc system for providing several two-dimensional x-ray projection images, the surface electrodes positions determination unit is adapted to determine the positions of the plurality of surface electrodes by performing a three-dimensional position modelling based on the several two-dimensional x-ray projection images, the cardiac structure position determination unit is adapted to match a non-patient specific generalized three-dimensional cardiac model with a cardiac contour in selected two-dimensional x-ray projection images from the several two-dimensional x-ray projection images, and the electrical activity map determination unit is adapted to determine the electrical activity map by performing an electrocardiographic mapping on the surface of the matched generalized three-dimensional cardiac model, thereby preferentially providing an approximate single beat, real time or near real time epicardial activation pattern with myocardial diagnostic capabilities ranging beyond current state-of-art ECG systems.

The projection images providing unit can also be a storing unit, in which the projection images are stored already and from which the projection images can be retrieved for providing the same. The projection images providing unit can also be a receiving unit for receiving the projection images via a wired or wireless data connection from a projection images acquisition unit like an x-ray C-arm system.

In a further aspect of the present invention a method for providing an electrical activity map of the heart of a living being by means of electrical signals from the heart acquired by a plurality of surface electrodes on an outer surface of the living being is presented, the method comprising:
    providing projection images of the heart and of the plurality of surface electrodes in different directions by a projection images providing unit,
    determining positions of the plurality of surface electrodes based on the provided projection images by a surface electrodes positions determination unit,
    determining a position of a cardiac structure of the living being based on the provided projection images by a cardiac structure position determination unit, wherein an anatomical cardiac model including the cardiac structure is adapted to the provided projection images of the heart, in order to determine the position of the cardiac structure,
    determining the electrical activity map at the cardiac structure based on the electrical signals measured on the outer surface of the living being, the determined positions of the plurality of electrodes and the determined position of the cardiac structure by an electrical activity map determination unit.

In a further aspect of the present invention a computer program for providing an electrical activity map of the heart of a living being by means of electrical signals from the heart acquired by a plurality of surface electrodes being arranged on an outer surface of the living being is presented, the computer program comprising program code means for causing a system as defined in claim 1 to carry out the steps of the method as defined in claim 9, when the computer program is run on a computer controlling the system.

It shall be understood that the system of claim 1, the method of claim 9 and the computer program claim 10 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
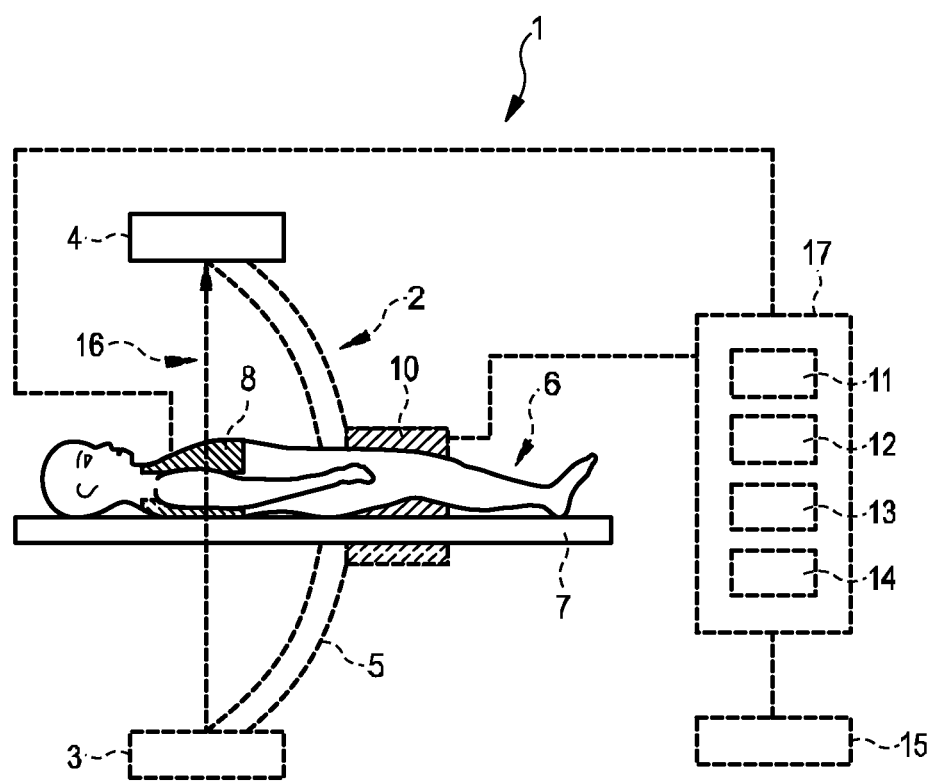
FIG. 1 shows schematically and exemplarily an embodiment of a system for providing an electrical activity map of the heart of a living being.
Figure 2:
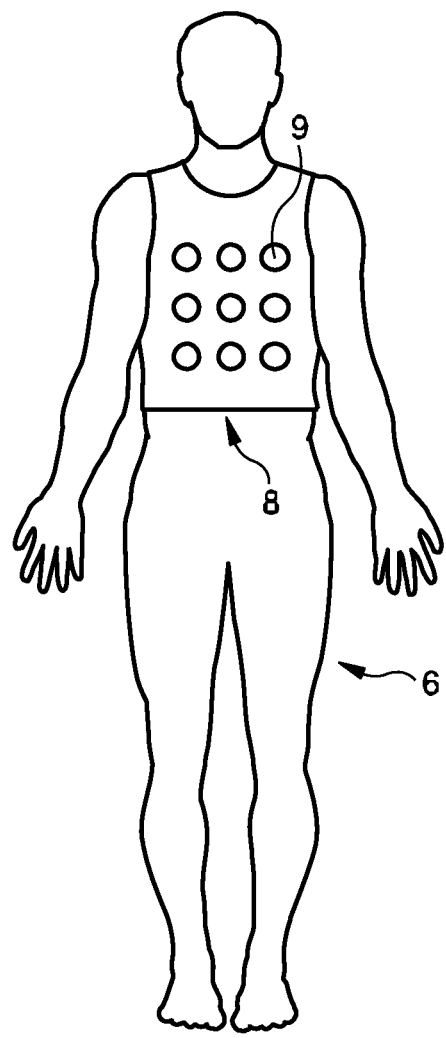
FIG. 2 shows schematically and exemplarily an embodiment of a vest comprising surface electrodes.

FIG. 1 shows schematically and exemplary an embodiment of a system for providing an electrical activity map of the heart of a living being by means of electrical signals from the heart acquired by a plurality of surface electrodes on an outer surface of the living being. In this embodiment, the living being is a person 6 lying on a table 7. The person 6 wears a vest 8, which is schematically and exemplary shown in FIG. 2. The vest 8 comprises a plurality of surface electrodes 9 that are in contact with the outer surface of the thorax of the person 6, in order to allow the surface electrodes 9 to acquire electrical signals, in particular, electrical potentials, at the outer surface. The vest 8 with the plurality of surface electrodes 9 is electrically connected to a determination system 17 comprising an electrical activity map determination unit 13 for transferring the electrical signals measured by the plurality of surface electrodes 9 to the electrical activity map determination unit 13.

It should be noted that the figures are not to scale. For instance, the surface electrodes 9 in the vest 8 shown in FIG. 2 have—relative to the dimensions of the person 6—a much smaller diameter. Moreover, the electrodes 9 in the vest 8 are only schematically and exemplarily indicated in FIG. 2, i.e., for instance, they can be distributed differently within the vest 8. The vest 8 preferentially comprises several hundreds of the surface electrodes 9 covering the entire thorax of the person. The vest 8 is tightly attached to the skin of the thorax by an adhesive. Alternatively or in addition, the vest can comprise elastic textiles for tightly fitting the vest to the skin of the thorax.

The system 1 comprises a projection images providing unit 2 for providing projection images of the heart and of the plurality of surface electrodes 9 in different directions. In this embodiment, the projection images providing unit 2 is an x-ray C-arm system. The x-ray C-arm system 2 comprises an x-ray source 3 for emitting an x-ray beam 16 traversing the vest 8 and the heart of the person 6. The x-ray beam 16 is preferably a substantially conical x-ray beam that is dimensioned such that the surface electrodes 9 and the heart of the person 6 can be within the x-ray beam. After the x-ray beam 16 has traversed the vest 8 and the heart of the person 6 it is detected by an x-ray detector 4. The x-ray detector 4 comprises a two-dimensional detection surface for generating two-dimensional projection images of the surface electrodes 9 and the heart of the person 6. The x-ray source 3 and the x-ray detector 4 are mounted on a C-arm 5, which is rotatable around the person 6 such that projection images can be acquired in different directions. The x-ray C-arm system 2 is controlled by a control unit 10, wherein the generated projection images are provided via the control unit 10 to the determination system 17. In another embodiment, the projection images can also be provided to the determination system 17 in another way. For instance, they can be transmitted to the determination unit not via the control unit 10, but directly or via another unit.

In this embodiment, the x-ray C-arm system 2 is adapted to perform a single axis C-arm movement, i.e. a rotational movement around the person 6 that is defined by a single rotational axis. However, in another embodiment the x-ray C-arm system can also be adapted to perform a dual axis C-arm movement, i.e. a movement that can be defined by rotations around two rotational axis.

In this embodiment, the x-ray C-arm system 2 is a monoplane projection system, wherein at a time only a single projection image can be acquired. In another embodiment, the x-ray C-arm system can also be a biplane projection system comprising two x-ray sources and two x-ray detectors, which are arranged such that simultaneously two projection images can be acquired in two orthogonal projection directions.

The determination system 17 comprises a surface electrodes positions determination unit 11 for determining the positions of the plurality of surface electrodes 9 on the outer surface of the person 6 based on the provided projection images. In particular, the surface electrodes positions determination unit 11 is adapted to model the positions of the surface electrodes 9 from the projection images, in order to determine the positions of the plurality of surface electrodes 9. For instance, a model distribution of surface electrodes can be provided and the generation of the provided projection images can be simulated for generating simulated projection images by forward projecting the model distribution, wherein the model distribution of the surface electrodes can be modified such that deviations between projected surface electrodes positions in the provided actual projection images and in the simulated projection images are minimized. The resulting modified model distribution of the surface electrodes can then define the surface electrodes positions. In another embodiment, other known methods for determining three-dimensional positions of an object from two or more two-dimensional projection images can be used by the surface electrodes positions determination unit for determining the positions of the plurality of surface electrodes on the outer surface of the person based on the provided projection images.

Before determining the positions of the plurality of surface electrodes on the outer surface of the person based on the provided projection images, the contrast of the projected surface electrodes in the provided projection images can be increased by performing a contrast enhancement technique. For instance, several projection images, which have been acquired in the same projection geometry and without an intermediate movement of the person, can be averaged, in order to enhance the visibility of the surface electrodes in the projection images. If the person has moved between the acquisition of two projection images to be averaged, reference markers visible in the two images can be used for registering these two images, before averaging the images.

The determination system 17 further comprises a cardiac structure position determination unit 12 for determining a position of a cardiac structure of the person 6 based on the provided projection images, wherein the cardiac structure position determination unit 12 is adapted to adapt an anatomical cardiac model including the cardiac structure to the provided projection images of the heart, in order to determine the position of the cardiac structure. In this embodiment, the cardiac structure is the epicardial surface of the heart such that the anatomical cardiac model at least includes the epicardial surface of the heart. The anatomical cardiac model is preferentially a non-person-specific cardiac model. Thus, the anatomical cardiac model is preferentially a general anatomical cardiac model which can be obtained, for example, by segmenting the heart in a plurality of medical images of a plurality of persons, thereby generating a plurality of segmented hearts, and by averaging this plurality of segmented hearts.

The cardiac structure position determination unit 12 is preferentially adapted to translate, rotate and scale the cardiac model such that the transformed cardiac model corresponds to the provided projection images. The cardiac structure position determination unit 12 can also be adapted to additionally deform the cardiac model, i.e. to modify the shape of the cardiac model, in order to adapt the cardiac model to the provided projection images. For instance, the cardiac model can be stretched or compressed in certain directions for adapting the cardiac model to the provided projection images.

In particular, the cardiac structure position determination unit 12 can be adapted to generate simulated projection images, which correspond to the provided projection images, by simulating projections through the transformed cardiac model in the projection acquisition geometry used for acquiring the actual provided projection images. The cardiac model can then be transformed such that at least regarding the epicardial surface deviations between the provided projection images and the simulated projection images are minimized.

The projection images, which are used for determining the position of the cardiac structure, in particular, the position of the epicardial surface, can be all provided projection images or only a selection of the provided projection images. The selection of provided projection images may include, for instance, a left anterior oblique projection image and a right anterior oblique projection image. However, also other projection images can be used for determining the position of the cardiac structure, in particular, the position of the epicardial surface.

The determination system further comprises the electrical activity map determination unit 13 for determining the electrical activity map at the cardiac structure, i.e., in this embodiment, on the epicardial surface, based on the electrical signals measured on the outer surface of the person 6, the determined positions of the plurality of surface electrodes 9 and the determined position of the cardiac structure. For determining the electrical activity map well known methods can be used like the methods disclosed in the article "Electrocardiographic Imaging (ECGI): A Noninvasive Imaging Modality for Cardiac Electrophysiology and Arrhythmia" by Ramanathan et al., Nature Medicine 10, 422-428 (2004) or disclosed in U.S. Pat. No. 7,471,971, which are herewith incorporated by reference. Moreover, known products from the companies CardioInsight Technologies and Amycard can be used for determining the electrical activity map at the cardiac structure, i.e. in this embodiment on the epicardial surface, based on the electrical signals measured on the outer surface of the person, the determined positions of the plurality of electrodes and the determined position of the cardiac structure.

The determination system 17 further comprises an analysis unit 14 for analyzing the electrical activity map for determining electrophysiological mechanisms of certain cardiac arrhythmias. Moreover, in addition or alternatively the analysis unit 14 may be adapted to analyze the electrical activity behaviour of cardiac dyssnychrony in heart failure patients as disclosed in the articles "Noninvasive Characterization of Epicardial Activation in Humans with Diverse Atrial Fibrillation Patterns" by P. S. Cuculich et al., Circulation 122, 1364-1372 (2010), "Electrocardiographic Imaging of Ventricular Bigeminy in a Human Subject" by Y. Wang et al., Circulation Arrhythmia and Electrophysiology 1, 74-75 (2008) and "Electrocardiographic Imaging of Cardiac Resynchronization Therapy in Heart Failure: Observations of Variable Electrophysiological Responses" by P. Jia et al., Heart Rhythm Journal 3, 296-310 (2006), which are herewith incorporated by reference.

In particular, the analysis unit can be adapted to perform at least one of following analyses based on the electrical activity map: determination of an anatomical position of ectopi foci, determination of an anatomical position of ventricular re-entries, distinguishing between re-entry or focal ventricular tachycardia and assessing of its localizations, assessing re-connection of pulmonary vein conduction and localization of culprit pulmonary veins, and assessment of effects of antiarrhythmic drugs.

The electrical activity map of the heart and optionally results of the analysis like determined anatomical positions of ectopic foci and ventricular re-entries can be shown on a display unit 15.

Figure 3:
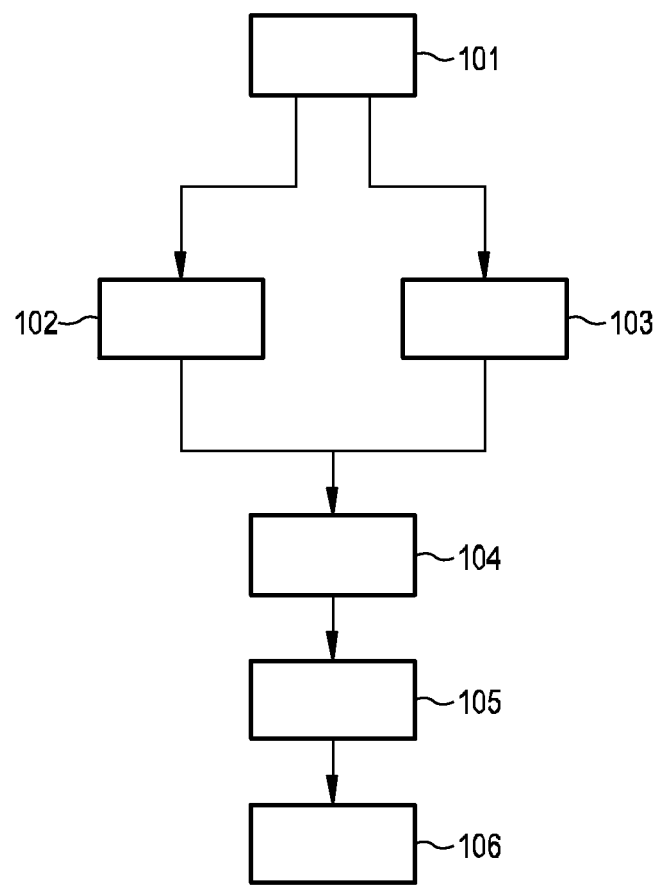
FIG. 3 shows a flowchart exemplarily illustrating an embodiment of a method for providing an electrical activity map of the heart of a living being.

In the following an embodiment of a method for providing an electrical activity map of the heart of a living being by means of electrical signals from the heart acquired by a plurality of surface electrodes on an outer surface of the living being will exemplarily be described with reference to a flowchart shown in FIG. 3.

In step 101, projection images of the heart and of the plurality of surface electrodes in different directions are provided by the projection images providing unit. For instance, an x-ray C-arm system is used for acquiring projection images of the heart and of the plurality of surface electrodes in different directions. In step 102, positions of the plurality of surface electrodes are determined based on the provided projection images by the surface electrodes position determination unit. In particular, the positions of the surface electrodes are modeled from the projection images, in order to determine the positions of the plurality of surface electrodes. In step 103, a position of a cardiac structure of the living being is determined based on the provided projection images by the cardiac structure position determination unit, wherein an anatomical cardiac model including the cardiac structure is adapted to the provided projection images of the heart, in order to determine the position of the cardiac structure. In this embodiment, the cardiac structure is the epicardial surface such that the position of the epicardial surface is determined by adapting an anatomical cardiac structure including the epicardial surface to the provided projection images of the heart. Steps 102 and 103 can be performed in an arbitrary order, i.e. they can be performed consecutively or simultaneously.

In step 104, the electrical activity map determination unit determines the electrical activity map at the cardiac structure, i.e., in this embodiment, on the epicardial surface, based on the electrical signals measured on the outer surface of the person, the positions of the plurality of surface electrodes determined in step 102 and the position of the cardiac structure determined in step 103. In step 105, the analysis unit analyzes the electrical activity map, in order to determine, for example, anatomical positions of ectopic foci and/or of ventricular re-entries. In step 106, the electrical activity map and optionally also results of the analysis like anatomical positions of ectopic foci and/or ventricular re-entries are shown on the display unit.

In the embodiment of the method for providing an electrical activity map of the heart described above with reference to FIG. 3 it is assumed that the electrical signals on the outer surface of the person have been measured already and are provided to the electrical activity map determination unit for allowing the electrical activity map determination unit to determine the electrical activity map. In another embodiment, the measurement of the electrical signals at the outer surface of the person can also be a part of the method for providing the electrical activity map, wherein in this case a corresponding electrical signals measurement step is performed before step 104.

Electrocardiographic mapping (ECM) is a method where body surface signals, i.e. electrical signals like electrical potentials measured at the outer surface of the person, which are measured by a multitude of electrodes covering the entire human thorax, are used to calculate the activation of the epicardial surface of the heart. The electrodes are surface electrodes, i.e. electrodes measuring electrical signals at the surface of the person, and they are contained in the vest that is tightly attached to the skin of the thorax by an adhesive. Since the position of the epicardial heart surface and the positions of the surface electrodes have been determined, the three-dimensional spatial relations between the epicardial heart surface and the surface electrodes are known. This enables the electrical activity map determination unit to compute an accurate single beat electrical activation pattern on the epicardial heart surface being the electrical activity map. The system described above with reference to FIG. 1 can therefore provide a non-invasive method for rapid assessment, i.e. within seconds to real time, of cardiac electrical activation. This electrocardiographic mapping can be performed, for example, during an electrophysiological procedure or during interventional cardiology procedures in a corresponding laboratory. However, the electrocardiographic mapping can also be performed for pre-interventional or post-interventional follow-up diagnostic procedures. In particular, the electrocardiographic mapping can be used to assess effects of antiarrhythmic drugs at certain points during a course of drug use and may be used for performing a high resolution electrocardiographic analysis.

The surface electrodes positions determination unit is preferentially adapted to perform a three-dimensional electrode position modelling from several two-dimensional x-ray projections of the x-ray C-arm system. The x-ray C-arm system is, for example, a Philips Allura Xper FD10 or FD20 system or a mobile x-ray C-arm system such as the Philips Veradius or BV systems. The x-ray C-arm system can be adapted to perform a biplane imaging for generating simultaneously two projection images, or it can be adapted to acquire two or more projection images by performing a monoplane C-arm imaging, wherein the surface electrodes positions determination unit can be adapted to determine the three-dimensional positions of all surface electrodes through three-dimensional modelling from two or more separate projection images being preferentially two-dimensional fluoroscopy or exposure x-ray images. The x-ray C-arm system can also be adapted to perform a dual axis C-arm movement, in order to move the x-ray source and the x-ray detector on an optimal trajectory to obtain all electrodes in selected x-ray frames for three-dimensional electrode position modelling.

The system described above with reference to FIG. 1 can be operated to determine the electrical activity map by only requiring a short C-arm acquisition protocol without any sterility requirements, i.e. the person does not need to be undressed et cetera, with very limited x-ray dose burden.

The cardiac structure position determination unit preferentially matches a non-patient-specific generalized three-dimensional cardiac model with the cardiac contour as imaged under different projection angles selected from the two-dimensional x-ray runs used for modelling the three-dimensional electrode positions. The electrical activity map determination unit preferentially performs an electrocardiographic mapping on the surface of the generalized cardiac model, in order to provide an approximate single beat epicardial activation pattern with myocardial diagnostic capabilities ranging far beyond known electrocardiography systems that only provide very course information about myocardial activation.

The system described above with reference to FIG. 1 provides an electrocardiographic mapping based on three-dimensional modelling of vest electrode positions by means of rapid C-arm imaging combined with matching of a generalized three-dimensional cardiac model. The system can therefore provide an electrocardiographic diagnostic tool that can be used for obtaining, for instance, pre-interventional and post-interventional information that is not obtainable by known electrocardiographic systems. For example, information can be provided such as reasonably accurate positions of ectopic foci, reasonable accurate positions of ventricular re-entries, information that distinguishes between re-entry or focal ventricular tachycardia and its localizations, information about re-connection of pulmonary vein conduction and localization of culprit pulmonary veins, in order to be at least able to distinguish between left and right pulmonary veins, and information about effects of antiarrhythmic drugs, in particuluar, of changes in use of antiarrhythmics drugs.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the surface electrodes positions, the determination of the cardiac structure position, the determination of the electrical activity map and the analysis of the electrical activity map performed by one or several units or devices can be performed by any other number of units or devices. For example, steps 102 to 105 can be performed by a single unit or by any other number of different units. The determinations and/or the analysis of the electrical activity map and/or the control of the system for providing an electrical activity map in accordance with the method for providing an electrical activity map can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a system for providing an electrical cardiac activity map by means of electrical signals acquired by a plurality of surface electrodes on an outer surface of a living being. A cardiac structure position determination unit determines a position of a cardiac structure, in particular, of the epicardial surface, based on the provided projection images, wherein an anatomical cardiac model is adapted to the projection images. An electrical activity map determination unit determines the electrical activity map at the cardiac structure based on the electrical signals, positions of the plurality of surface electrodes also determined from the projection images and the determined position of the cardiac structure. This allows determining the electrical activity map at the cardiac structure with high accuracy, without necessarily needing, for instance, an x-ray computed tomography system that would apply a relatively high x-ray radiation dose to the living being.

The invention claimed is:

1. A system for providing an electrical activity map of the heart of a living being by means of electrical signals from the heart acquired by a plurality of surface electrodes on an outer surface of the living being, the system comprising:
   a projection images providing unit for providing projection images of the heart and of the plurality of surface electrodes in different directions, a surface electrodes positions determination unit for determining positions of the plurality of surface electrodes on the outer surface of the living being based on the provided projection images, a cardiac structure position determination unit for determining a position of a cardiac structure of the living being based on the provided projection images, wherein the cardiac structure position determination unit is configured to adapt an anatomical cardiac model including the cardiac structure to the provided projection images of the heart, in order to determine the position of the cardiac structure, and an electrical activity map determination unit for determining the electrical activity map at the cardiac structure based on the electrical signals measured on the outer surface of the living being, the determined positions of the plurality of surface electrodes on the outer surface of the living being and the determined position of the cardiac structure.

2. The system of claim 1, wherein the surface electrodes positions determination unit is configured to provide a model distribution of the surface electrodes, to adapt the model distribution to the provided projection images, and to determine the positions of the plurality of surface electrodes from the adapted model distribution.

3. The system as defined in claim 1, wherein the cardiac model is a non-specific cardiac model.

4. The system of claim 3, wherein the non-specific cardiac model is not specific to the heart of the living being.

5. The system as defined in claim 3, wherein the cardiac structure position determination unit is configured to adapt the anatomical cardiac model including the cardiac structure to the provided projection images of the heart by performing at least one of a translation procedure, a rotation procedure and a scaling procedure.

6. The system as defined in claim 1, wherein the projection image providing unit is an x-ray C-arm system.

7. The system of claim 5, wherein the non-specific cardiac model is a segmented heart model comprising an average of a plurality of segmented heart images of a plurality of persons.

8. The system as defined in claim 6, wherein the x-ray C-arm system is configured to perform a single axis C-arm movement or a dual axes C-arm movement.

9. The system as defined in claim 6, wherein the x-ray C-arm system is a monoplane projection system or a biplane projection system.

10. The system as defined in claim 1,
wherein the anatomical cardiac model is a non-patient specific generalized three-dimensional cardiac model,
wherein the projection images providing unit is a C-arc system for providing several two-dimensional x-ray projection images,
wherein the surface electrodes positions determination unit is configured to determine the positions of the plurality of surface electrodes by performing a three-dimensional position modelling based on the several two-dimensional x-ray projection images,
wherein the cardiac structure position determination unit is configured to match the non-patient specific generalized three-dimensional cardiac model with a cardiac contour in selected two-dimensional x-ray projection images from the several two-dimensional x-ray projection images, and
wherein the electrical activity map determination unit is configured to determine the electrical activity map by performing an electrocardiographic mapping on the surface of the matched generalized three-dimensional cardiac model.

11. The system of claim 1, wherein the projection images providing unit is a storage unit in which the projection images are stored.

12. The system of claim 1, wherein the plurality of surface electrodes comprises at least one hundred electrodes, and wherein the electrical activity map determination unit is configured to receive the electrical signals from the at least one hundred electrodes.

13. A method for providing an electrical activity map of the heart of a living being by means of electrical signals from the heart acquired by a plurality of surface electrodes on an outer surface of the living being, the method comprising:
providing projection images of the heart and of the plurality of surface electrodes in different directions by a projection images providing unit,
determining positions of the plurality of surface electrodes on the outer surface of the living being based on the provided projection images,
determining a position of a cardiac structure of the living being based on the provided projection images by adapting an anatomical cardiac model including the cardiac structure to the provided projection images of the heart, in order to determine the position of the cardiac structure,
determining the electrical activity map at the cardiac structure based on the electrical signals measured on the outer surface of the living being, the determined positions of the plurality of electrodes on an outer surface of the living being, and the determined position of the cardiac structure.

14. The method of claim 13, wherein providing projection images of the heart and of the plurality of surface electrodes in different directions by a projection images providing unit comprises:
emitting an x-ray beam from an x-ray source to traverse the electrodes and the heart; and
detecting with an x-ray detector the x-ray beam after the x-ray beam has traversed the electrodes and the heart.

15. The method of claim 14, further comprising rotating the x-ray source and x-ray detector around the living being in a single rotational axis to acquire the projection images in the different directions.

16. The method of claim 14, further comprising rotating the x-ray source and x-ray detector around the living being in two rotational axes to acquire the projection images in the different directions.

17. The method of claim 13, wherein providing projection images of the heart and of the plurality of surface electrodes in different directions by a projection images providing unit comprises:
emitting a first x-ray beam from a first x-ray source to traverse the electrodes and the heart in a first direction;
detecting with a first x-ray detector the first x-ray beam after the first x-ray beam has traversed the electrodes and the heart in the first direction;
emitting a second x-ray beam from a second x-ray source to traverse the electrodes and the heart in a second direction orthogonal to the first direction; and
detecting with a second x-ray detector the first x-ray beam after the first x-ray beam has traversed the electrodes and the heart in the second direction.

18. The method of claim 13, wherein determining positions of the plurality of surface electrodes on the outer surface of the living being based on the provided projection images model distribution of the surface electrodes comprises:

adapting a model distribution of the surface electrodes to the provided projection images; and determining the positions of the plurality of surface electrodes from the adapted model distribution.

19. The method of claim 13, wherein the anatomical cardiac model is a non-patient specific generalized three-dimensional cardiac model, wherein determining the positions of the plurality of surface electrodes on the outer surface of the living being comprises performing a three-dimensional position modelling based on the several two-dimensional x-ray projection images, wherein adapting the anatomical cardiac model including the cardiac structure to the provided projection images of the heart in order to determine the position of the cardiac structure includes matching the non-patient specific generalized three-dimensional cardiac model with a cardiac contour in selected two-dimensional x-ray projection images from the several two-dimensional x-ray projection images, and wherein determining the electrical activity map at the cardiac structure includes performing an electrocardiographic mapping on the surface of the matched generalized three-dimensional cardiac model.

20. A non-transitory computer readable medium having stored thereon computer-readable instructions for causing a system to perform a method for providing an electrical activity map of the heart of a living being by means of electrical signals from the heart acquired by a plurality of surface electrodes on an outer surface of the living being, the method comprising:

providing, via a projection images providing unit of the system, projection images of the heart and of the plurality of surface electrodes in different directions, determining positions of the plurality of surface electrodes based on the provided projection images, determining a position of a cardiac structure of the living being based on the provided projection images by adapting an anatomical cardiac model including the cardiac structure to the provided projection images of the heart, in order to determine the position of the cardiac structure, and determining the electrical activity map at the cardiac structure based on the electrical signals measured on the outer surface of the living being, the determined positions of the plurality of electrodes and the determined position of the cardiac structure.

* * * * *